United States Patent [19]

Grandadam et al.

[11] 4,206,757
[45] Jun. 10, 1980

[54] DEVICE FOR THE ADMINISTRATION OF MEDICINAL SUBSTANCES

[75] Inventors: Jean A. Grandadam, Saint-Maur des Fosses; Daniel Benet, Villemomble; Alain Jobard, Le Blanc-Mesnil, all of France

[73] Assignee: Roussel-Uclaf, Paris, France

[21] Appl. No.: 913,015

[22] Filed: Jun. 6, 1978

[30] Foreign Application Priority Data

Jun. 8, 1977 [FR] France ............... 77 1717525

[51] Int. Cl.² .............................................. A61M 7/00
[52] U.S. Cl. .................................................. 128/260
[58] Field of Search ............... 128/253, 260, 261, 264, 128/329 R, 330, 213, 223, 268; 119/156; 40/301

[56] References Cited

U.S. PATENT DOCUMENTS

| 495,270 | 4/1893 | Rozell | 40/301 |
|---|---|---|---|
| 2,568,207 | 9/1951 | Spicher | 128/260 |
| 3,405,688 | 10/1968 | Gerhardi | 119/156 |
| 3,595,201 | 7/1971 | Dumas | 128/330 |
| 3,788,296 | 1/1974 | Klatt et al. | 128/268 |
| 3,942,480 | 3/1976 | Hair et al. | 119/156 |
| 3,949,708 | 4/1976 | Meeks | 119/156 |
| 4,026,290 | 5/1977 | Broorer et al. | 128/268 |
| 4,041,946 | 8/1977 | Barton | 128/260 |

FOREIGN PATENT DOCUMENTS 169135 10/1921 United Kingdom ............... 40/301

Primary Examiner—Robert W. Michell
Assistant Examiner—C. F. Rosenbaum
Attorney, Agent, or Firm—Bacon & Thomas

[57] ABSTRACT

A flexible cup contains a medicinal substance and the open face of the cup is pressed against a subject's ear skin by a pin passing through the cup and ear. A compensating member on the end of the pin presses the ear into the cup to maintain contact with the medicinal substance.

5 Claims, 16 Drawing Figures

DEVICE FOR THE ADMINISTRATION OF MEDICINAL SUBSTANCES

BACKGROUND OF THE INVENTION

The present invention relates to a device for the administration of medicinal substances. More particularly, a device to be applied to the skin of the ear of a subject, especially of an animal.

Numerous means for the administration of medicinal substances, especially to animals, are known. These devices may be applied to the skin of different parts of the body, such as the ears, the neck, the shoulder, the tail or the nasal cavities, or again the mucosa of the genital organs of a subject. These known means are in different forms, such as adhesive tape, receptacles of different types, perforating plates. These known means are maintained in place, for example, by adhesives or with the aid of different mechanical devices, such as clips, fasteners, pins, spikes or clamps. It was found that the use of the devices of the prior art was not always satisfactory with respect to the maintenance in place, the tightness and the optimum penetration of the medicinal substance to be administered. Thus, for example, the fixation of such means with the aid of an adhesive often requires the initial shaving of the hair and cleaning of the skin and in addition to bond frequently did not resist all of the exigencies of the life of the subject. Means maintained in place with the aid of mechanical devices, even if they are kep in place better, do not always achieve a satisfactorily tight bond between said means and the skin. The mechanical means do not insure the permanent contact between the surface of skin intended to enter into contact with the medicinal substance, which is indispensable for optimum absorption. This inconvenience is often encountered when the medicinal substances to be applied are in the form of ointments, cream or gels. Some of the known means have attempted to solve this problem of the application of substances having the consistency of cream, ointments or gels by using aluminum cups as the receptacles, the cups being attached to the ear of the subject by means of a pin. Even though the cup is deformed during its placement, after the operation of placement, it retains the form and volume received. Because of this fact, the layer of the medicinal substance initially in contact with the skin is absorbed and a space is created between the absorbent surface of the skin and the substance in question, which is contained in the cup. There is, therefore, a risk that the medicinal substances remains partially unabsorbed. Another known means consists of a cup of a plastic material, of a more or less elastic nature, which is secured to the ear of the subject with several pins. The medicinal substance is introduced in the form of a solution previously adsorbed on a solid support, such as a porous disk of burned clay. After the placing of this means of administration, the solid support rests in the cup and is maintained in permanent contact with the skin by a spring resting against the bottom of said cup. As a result, even if the cup is made of an elastic material, the potential elasticity of the cup never has the effect of moving the bottom of the cup closer to the skin. This potential elasticity, therefore, serves only to assure the contact of the edge of the cup with the skin. This means of administration is suitable only in the case of a solid support which previously had adsorbed a medicinal solution. Consequently, it is obvious that in the case where a medicinal substance having the consistency of an ointment, a cream or a gel must be administered such a means of administration cannot be used. (French Pat. No. 2 292 489 and U.S. Pat. No. 3,788,296 describe a device for the application of a medicinal substance to the skin of an animal.

Devices used to mark the animals which comprend a pin through the skin are described in U.S. Pat. No. 1,390,342 and French Pat. Nos. 335 245, 740 203, and 858 267)

SUMMARY OF THE INVENTION

The device of the present invention was developed to remedy the difficulties described above. Nevertheless, in the course of its development it was found that when a medicinal substance in the form of a pharmaceutical preparation having the consistency of an ointment, a cream or a gel, is administered contained in a receptacle applied to the skin of the ear of a subject, a free space is formed between the absorbent surface of the skin and said medicinal substance, after the layer of said substance placed in contact with the skin has been absorbed. This fact interferes with the regular and complete process of absorption of the medicinal substance on the one hand and on the other, may cause harmful changes on the absorbent surface of the skin, such as the formation of a scab.

Therefore, in order to be able to successfully administer through the skin of the ear of a subject a medicinal substance in the form of a pharmaceutical preparation having the consistency of an ointment, a cream or a gel, it is necessary to employ a device capable of assuring the permanent contact of such a substance with the surface of the skin of a subject. The device which is the object of the present invention, is based on the fact that a permanent contact between said medicinal substance to be administered and the surface of the skin of a subject may be assured successfully only in the case where the structural elements of the device are exposed to pressure, having the effect of urging said substance against the surface of the skin.

The device for the administration of medicinal substances which is the object of the present invention and is useful in medicine, comprises a means of fastening to the skin of the ear of the subject, such as a pin or a spike serving both to maintain the assembly of the device and its maintenance in place and is characterized by the fact that it comprises further:

a hollow cup to receive the medicinal substance, said hollow cup being deformable elastically when subjected to pressure, and compensating means capable of exercising, directly or otherwise, pressure on the hollow cup and simultaneously on the skin of the subject to cause the means to penetrate into the hollow cup and to maintain said pressure.

The device may be further characterized by the following items:

the hollow cup is an integral part of the fastening means;

the hollow cup consists of a piece which is independent of the fastening means, the piece being joined to said means before or after the placing of the device;

the compensating means consists of an elastic element, capable of receiving the fastening means;

the compensating means comprises two distinct elements, the first being an elastic element proper and the second a support capable of receiving the fastening means;

- the return piece (or compensating means) is constituted by a resilient dome cut out in the form of a rosette of which the "petals" are fairly numerous,
- the wall of the hollow dome (or hollow cup) containing the medicinal substance is provided with one or more concentric grooves,
- the wall of the hollow dome containing the medicinal substance is partially cut out at its periphery,
- the hollow dome containing the medicinal substance comprises one or more reduced areas situated between its top and its rim, and
- the fixing means is provided, in its portion intended to be placed in the return piece, with a thread and its opposite enlarged end is in the form of a polyhedron.

The device of the present invention functions as described hereafter. Because of the choice of the elements of the device of the invention and their arrangement, the hollow cup after its placement, has its edge in contact with the skin of the subject, while the compensating means exerts pressure on the wall of said hollow cup. The latter in turn exerts pressure on the medicinal substance contained in it. Simultaneously, the skin of the subject is pushed toward the inside of the hollow cup. At the rate at which the layer of the medicinal substance placed in contact with the surface of the skin, is absorbed by the latter, a new quantity of the medicinal substance is, under the pressure of the cup, moved toward the skin, thus replacing the layer absorbed. In this manner, permanent contact between the medicinal substance and the skin is assured.

It may be said that the bollow cup of the device of the present invention acts in the manner of the membrane of a pump, for example, which constantly moves the medicinal substance toward the abosrbent surface of the skin by pressure. Because of this, absorption takes place under optimum conditions and may be continued, if desired, until the medicinal substance contained in the hollow cup is exhausted.

Research has demonstrated also that if the skin, through which the absorption is to take place, is simultaneously urged toward the inside of the hollow cup, the contact between the skin and the cup is further improved, which insures improved tightness of fit of the device. It should also be mentioned that upon the penetration of the skin into the hollow cup, it stretches and becomes more capable of absorption. The device of the invention provides, as mentioned above, an excellent yield of absorption of a medicinal substance and by the same token is of considerable economic interest, the more so, since with previous devices the medicinal substance is frequently not absorbed in its entirety, resulting in a significant loss. It is equally important to take into consideration the fact that it is difficult to observe and to study the action of a medicinal substance if all of the amount administered has not been absorbed. This may happen frequently with the prior means of administration.

The device of the invention has also the advantage of easy removal from the subject. The ease with which this may be accomplished permits ready control of the duration of the absorption of the medicinal substance and the verification of the amounts absorbed. The absorption of a given substance may thus be interrupted at any moment, according to need.

The device further eliminates the inconvenience inherent particularly in devices already known and applied to the nasal cavities, the inconvenience being represented by the danger of such a device coming into contact with food and more particularly with liquids ingested by the subject. This results in a loss of said medicinal substance that is difficult to control. In the embodiment of the invention, the hollow cup may be an integral part of the fastening means or again it may consist of a piece independent of the fastening means. The term "to be an integral part" used in the foregoing refers to the part of the device of the invention that is obtained after machining or, in the alternate case, an assembly ready for use. The term includes an embodiment in which the hollow cup and the fastening means are produced by machining in a single piece, either of the same or different materials. This single piece may be made, for example, by casting. In this case, the material and the thickness of the wall of the cup is selected so that it is able to perform the function assigned to it, i.e. to deform elastically. Concerning the fastening means, if it is made of the same material as the hollow cup, its diameter is chosen to assure the rigidity necessary for the placement of the device of the invention. In the case where the fastening means is made of a material different from that of the hollow cup, the choice of its dimensions depends only on the arrangement of the device.

In a second embodiment of the device of the invention, the term "to be an integral part" may denote a hollow cup made separately from the fastening means, and which is then securely attached to said fastening means, following the fabrication of the latter.

In a third embodiment the hollow cup is not an integral part of the fastening means; it is made as an independent piece and is not combined with the fastening means until immediately prior to the use of the device.

The hollow cups of the different embodiments, once made, are filled with a pharmaceutical composition. They are then conditioned to be ready for distribution and application. After conditioning, the pharmaceutical composition contained in the hollow cup is covered, for example, by a protective film, which is removed prior to use.

The hollow cup is made of a material capable of elastic deformation under the effect of the pressure of the compensating means, thus allowing the wall of the cup to approach the skin and to reduce, in the majority of cases, the volume of the cup. This material may consist of a plastic having the necessary properties of elastic deformability, such as a natural or synthetic elastomer, polyvinyl chloride, polyethylene, polypropylene or nylon.

In a fourth embodiment, the compensating means, as mentioned above, may consist in one embodiment of an elastic element, designed in a manner so as to be capable of simultaneously receiving the fastening means.

In a fifth embodiment, the compensating means comprises two distinct elements, one of which is the elastic element proper and the other a support designed to receive the fastening means. The two pieces are assembled immediately preceding their use following the placement of the device of the invention. They may also be assembled at any time between their making and their use.

In a sixth embodiment of the present invention the return piece being constituted by a resilient dome is cut out in the form of a rosette. By way of example it is associated, by a fixing means, with a hollow dome as described above.

Such a return piece, while fulfilling its role of exerting pressure on the hollow dome, permits the blood circulation in the ear of the subject to take place under excellent conditions. The risks of circulatory disorders, even very slight ones in the blood vessels in this region of the skin are therefore eliminated.

The number of "petals" of the rosette can vary according to the material used and according to the desired pressure. By way of example this number can be from three to sixteen.

So as to facilitate maintenance of the point of the fixing means the return piece can be provided, in its central portion intended to allow passage of the said point, with several abutments.

When the point has passed through the return piece the abutments force it to remain in the established position and thus ensure that the device is maintained in place. These abutments can also be advantageously replaced by a thread.

In a seventh embodiment of the present invention the return piece described above can be associated with a hollow dome provided with one or more concentric grooves.

Hence, such a hollow dome which has a wall which is thinner at the place where a concentric groove is disposed, becomes more supple and responds better to the stresses due to the pressure exerted by the return piece.

By way of example the wall of this hollow dome can be provided with two concentric grooves.

In an eighth embodiment of the present invention the return piece described above is associated with a hollow dome of which the wall is partly cut out at its periphery.

The depth of these cut-outs is selected depending upon the qualities of the material from which the hollow dome is made and upon the resilience which it is desired to give to it, so that it can exert a desired pressure upon the medicinal substance.

By way of example the depth of these cut-outs in the wall can vary between one-fifth and two-thirds of the radius of the dome. The number of cut-outs can vary between, for example, two and thirty two.

This way of making the hollow dome, while ensuring regulation of the pressure exerted by the latter on the medicinal substance contained therein, also enables the contact between the said substance and the skin of the subject to be improved.

This type of dome is especially very useful in the case in which the medicinal substance is in the form of an ointment of thick consistency.

In a ninth embodiment of the present invention the return piece described above is associated, by a fixing means, with a hollow dome of which the wall comprises one or more reduced areas situated between its top and its rim.

This reduced area of the hollow dome thus makes it more supple and capable of responding more easily to the pressure exerted by the return piece and at the same time of improving the transfer of this pressure to the medicinal substance contained therein.

In a tenth embodiment of the present invention a hollow dome and a return piece, as described above, can be associated by a fixing means of which the portion intended to be placed in the return piece is provided with a thread.

This manner of making up the fixing means such as, for example, a spike, enables once the device has been placed, the pressure of the return piece on the said hollow dome to be readjusted, increased or reduced and permits the two members in question to be brought closer together or separated, by shortening or increasing the distance between the tops of the said members by screwing or unscrewing the said fixing means.

During screwing or unscrewing of the said fixing means the screw thread with which it is provided, given the nature of the material from which the return piece is made, can easily be engaged with and screwed into the abutments of the said return piece.

The central portion of the return piece in which is placed the fixing means can also, as already stated, be provided with a thread in place of abutments, corresponding to the thread with which the fixing means is provided. The readjustment of the pressure exerted by the return piece on the hollow dome will also be easy.

To facilitate screwing or unscrewing of the said fixing means its enlarged end opposite the threaded portion which can be called the head is made in the form of a polyhedron, such as the tri, tetra, penta or hexahedron.

This method of working can be useful espeically when, after the subject has carried the device of the invention for a fairly long time, it is desired, at a given moment, to readjust the pressure which the hollow dome exerts upon the medicinal substance in the form of an ointment which it contains.

In the case in which the fixing means is, for example, a spike, the head of which is round, the diameter of this head can vary.

By way of example in the embodiments in the device of the present invention the diameter of this head can be greater than the diameter of the body of the spike by an amount of from one fifth greater up to twice as great or even more.

The compensating means is made of a material having the elastic properties required to exercise the pressure on the hollow cup necessary to make the wall of said cup approach the skin. Because of this, the hollow cup is able to exercise a constant pressure upon the substance to be administered. This pressure force is also necessary to urge the skin into the cup. Such a material may consist, for example, of an elastic plastic substance, or a material of a metallic character, such as steel, a bronze or various other alloys. The pressure exerted by the compensating means being on the skin of the subject on the one hand and on the hollow cup on the other, consequently the pressure exerted by the hollow cup on the medicinal substance contained in the cup, must be in equilibrium. This equilibrium depends on the choice of materials used for the hollow cup and the compensating means and also on the consistency of the pharmaceutical composition including the medicinal substance to be administered. The force of the pressure to which the hollow cup is exposed following the placement of the device, is chosen by taking into account that at the rate at which medicinal substance is absorbed, the hollow cup urges new quantities of said substance toward the skin, under the effect of the compensating means. As a result, because the hollow cup is approaching the skin, the compensating means is extended and at the same time the pressure exerted by it, diminishes. It is important that the force of the pressure exerted by the compensating means be dimensioned with care so that it will be capable of performing its function from the placement of the device to the rate of absorption of the medicinal substance. The choice of the pressure that must be provided by the compensating means, the thickness of the skin of the ear of the subject, the elastic deformability of the hollow cup and its dimensions, the consistency of the pharmaceutical composition, together with the length of the fastening means chosen, play important roles in the design and the use of the device of the invention. It is also important, that the pressure exerted by the compensating means on the skin of the subject and on the hollow cup, and consequently, by the edge of said cup on the skin of the ear, be chosen, in addition to the criteria already mentioned, by taking into account the blood circulation in the part of the skin of the ear outlined by the device of the invention, after its placement. Excessive pressure by the compensating means could cause serious circulatory problems in the blood vessels of this region of the skin and provoke, in an extreme case, the onset of necroses.

As an example of an embodiment of the device of the invention, the hollow cup may have a thickness of 1 to 2 mm, an internal diameter of at the base of approximately 30 mm, an edge thickness of approximately 5 mm, a height of approximately 10 to 15 mm, which together yield a capacity of approximately 3 cm$^3$.

Concerning the compensating means, the internal diameter of the base of the cup must be taken into account, so that the skin of the ear may fold slightly under the effect of the pressure and penetrate into the hollow cup, without otherwise risking a "fracture" of the ear in relation to the edge of the cup. The bend of the skin of the ear after its penetration into the cup should be gentle in order to prevent the circulatory troubles already mentioned and to provide a good application of the edge of the cup against the skin, together with a satisfactory tightness of the device. If the condition of maximum tightness is not satisfied, leaks of the medicinal substance may develop at that location, given the pressure under which said substance is maintained in the cup. In order to satisfy these requirements, the diameter of the part of the compensating means which makes contact with the skin of the subject should, in general, be less than the internal diameter of the base of the hollow cup. Its order of magnitude may vary, for example, from 2/10 to 9/10 of said internal diameter of the base of the hollow cup. One may, therefore, as an example, determine that satisfactory results may be obtained with a compensating means having a part which enters into contact with the skin of the ear, with a thickness of 10 mm, and a diameter comprised between 5/6 and $\frac{1}{3}$ of the internal diameter of the hollow cup. Such a device is constituted by a hollow cup with an internal base diameter of 30 mm, and a compensating means having a diameter of the part entering into contact with the skin of between 25 and 10 mm, the thickness of the ear being approximately 10 mm. The height of the compensating means is chosen as a function of the design of the piece, the nature of the material of which it is made and the force of the pressure it is to exert on the hollow cup and on the skin. In the case of the device described above, it is of the order of 10 to 25 mm. The length of the fastening means, in the form of a pin, for the example presented in the foregoing, is of the approximate order of magnitude of 30 to 40 mm. In any case, it should be chosen as a function of the height of the compensating means, the thickness of the skin of the ear, the height of the hollow cup and also of the pressure exerted by the compensating means on the hollow cup. The placement of the device of the invention may be effected with the aid of a clip, such as those used to mark the animals. In the case where the hollow cup is an integral part of the fastening means, the placing of the device of the invention may be performed without any preliminary operation. In contrast, in a case where the hollow cup is provided, after manufacturing, in the form of a single piece, independent of the fastening means, it is necessary to place the device of the invention first and then combining said means with the latter, by placing it upon the device. Once the device of the invention is put in place, it may be easily removed at any time. It is sufficient for the purpose to cut, with the aid of pliers, the end of the fastening means placed at the side opposite to the hollow cup. Due to the arrangement of the device of the invention and its elasticity, the end of the fastening means may be disengaged by a simple pressure upon said device and the cutting operation performed with ease.

BRIEF DESCRIPTION OF THE DRAWINGS

The attached drawings illustrate, as examples, the schematized embodiments of the device which is the object of the invention. In the drawings, in order so that the different elements of the device of the invention may be clearly distinguished, together with their arrangement, the dimensions and proportions being somewhat exaggerated.

In the drawings.

Figure 1:
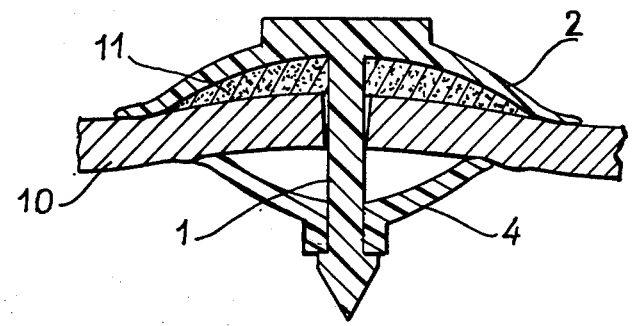
FIG. 1 is a diagrammatic view of one embodiment of the device of the invention in which the hollow dome and the fixing means are made in a single piece and in the same material, whereas the return piece constituted by a resilient return piece is in the form of a resilient dome serving simultaneously as support in which is placed the said fixing means, the two pieces being arranged one on each side of the skin of the ear.
Figure 2:
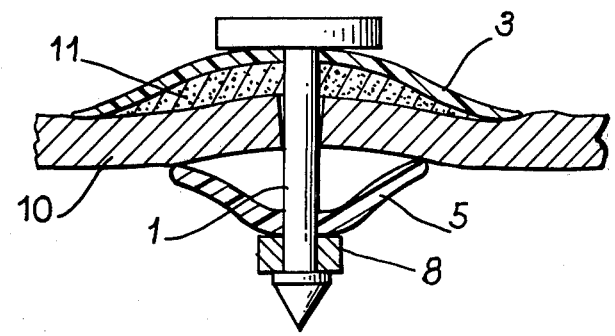
FIG. 2 is a diagrammatic view of an embodiment of the present device in which the hollow dome is an independent piece and the return piece constituted by a resilient return member is in the form of a resilient dome provided with an independent support, for receiving the fixing means. The two pieces are arranged one on each side of the skin of the ear.
Figure 3:
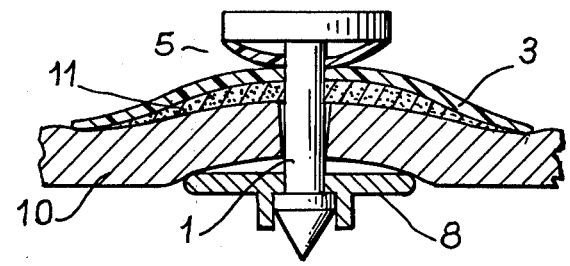
FIG. 3 is a diagrammatic view of an embodiment of the present device in which the hollow dome and the resilient return member, being independent pieces, are placed on the same side of the skin of the ear; the support for receiving the fixing means is also an independent piece and is mounted against the skin of the other side of the ear.
Figure 4:
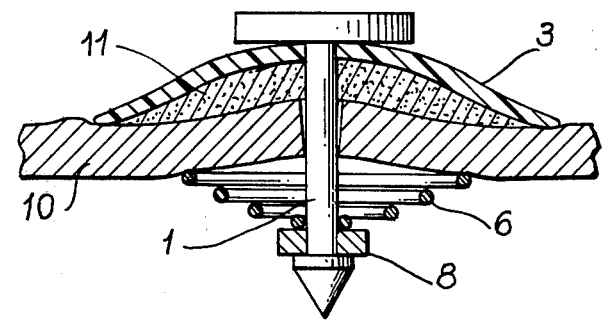
FIG. 4 is a diagrammatic view of an embodiment of the present device similar to that in FIG. 2, in which the resilient return member is in the form of a spring.
Figure 5:
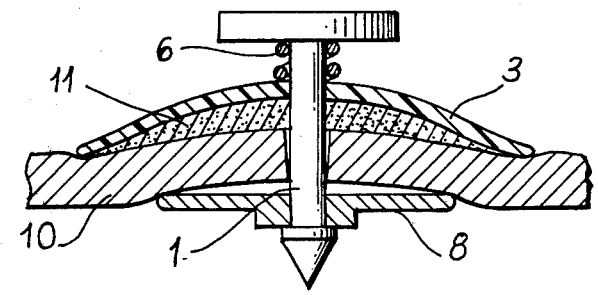
FIG. 5 is a diagrammatic view of an embodiment of the present device, similar to that in FIG. 3, in which the resilient return member is a spring mounted on the hollow dome.
Figure 6:
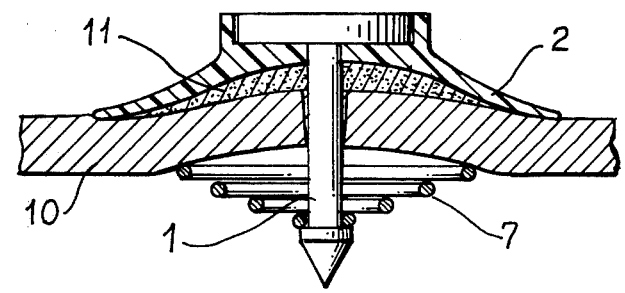
FIG. 6 is a diagrammatic view of an embodiment of the present device, similar to that in FIG. 1, in which the hollow dome, being worked as an independent piece, is then associated finally with the fixing means after working and the resilient return member is in the form of a spring arranged so as to be capable of serving simultaneously as support in which is placed the fixing means.
Figure 7:
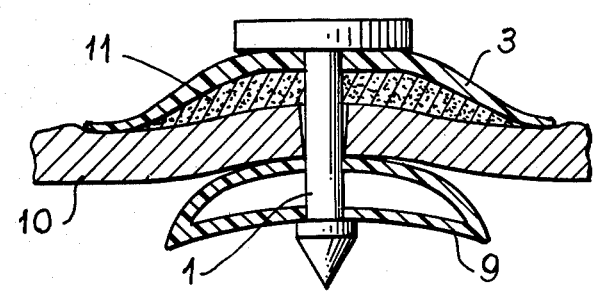
FIG. 7 is a diagrammatic view of an embodiment of the present device, similar to that in FIG. 2, in which the resilient return member is in the form of a resilient dome of which the base is closed and is adapted to receive the fixing means.
Figure 8:
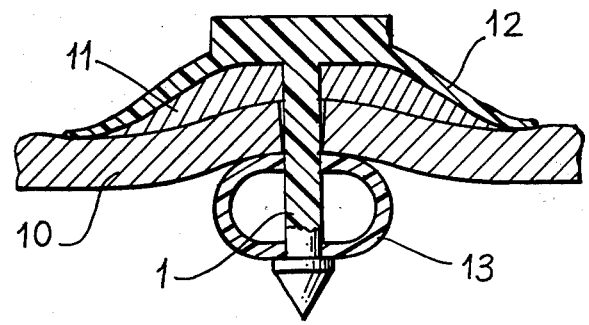
FIG. 8 is a diagrammatic view of the present device in which the hollow dome and the fixing means are made during working in one piece; the resilient return member is in the form of a resilient bulb arranged so as to be capable of serving simultaneously as support in which is placed the fixing means, the two pieces being placed one on each side of the skin of the ear.

1 represents the fixing means;

2 the hollow dome being made during working in single piece with the fixing means;

3 the hollow dome constituted by an independent piece;

4 the return piece constituted by a resilient return piece in the form of a resilient dome serving simultaneously as support in which is placed the fixing means 1;

5 the return piece constituted by a resilient return member in the form of a hollow dome requiring a separate support in which is placed the fixing means 1;

6 the return piece constituted by a resilient return member in the form of a spring requiring a separate support in which is placed the fixing means 1;

7 the return piece constituted by a resilient return member in the form of a spring adapted at one of its ends so as to be capable of serving simultaneously as a support in which is placed the fixing means 1;

8 the support in which is placed the fixing means constituted by an independent piece;

9 the return piece constituted by a resilient return member in the form of a dome of which the base is closed, serving simultaneously as support in which is placed the fixing means 1;

10 the skin of the ear of the subject;

11 the medicinal substance to be administered in the form of a pharmaceutical preparation having the consistency of an ointment, a cream or a jelly;

12 the hollow dome worked as an independent piece which is then associated finally after working with the fixing means to form a single piece;

13 the return piece constituted by a resilient return member in the form of a resilient bulb arranged so as to be capable of serving simultaneously as support in which is placed the fixing means;

14 the return piece constituted by a resilient dome cut out in the form of a rosette;

15 the head of the fixing means of which the diameter is reduced by comparison with the diameter of the head of the fixing means appearing in FIGS. 1 to 8;

16 the abutments with which the central portion of the return piece 14 is provided;

17 the hollow dome provided with the concentric grooves 18;

19 the head of the fixing means in the form of a hexahedron;

20 the thread with which the fixing means is provided in its portion intended to be placed in the central portion of the return piece 14;

21 the hollow dome comprising a reduced area 22 (of a slight thickness);

23 the hollow dome partially cut out at its periphery.

Figure 9:
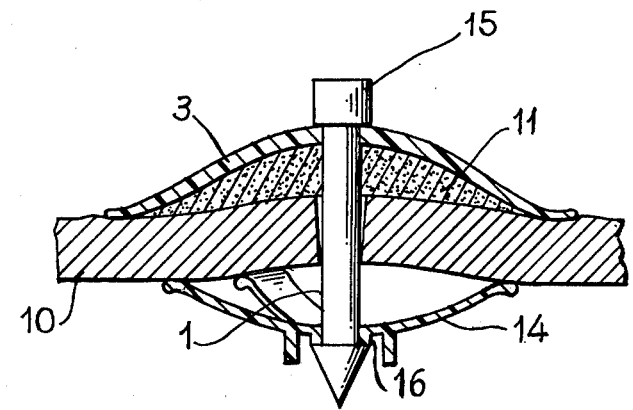
FIG. 9 is a diagrammatic view in section of an embodiment of the device of the invention in which the return piece is in the form of a resilient dome cut out in the form of a rosette; the hollow dome is one of those described above.
Figure 10:
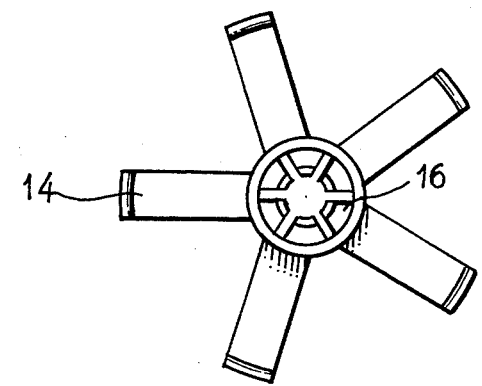
FIG. 10 is a diagrammatic view in projection of the return piece (a dome cut out in the form of a rosette) represented in FIG. 9.
Figure 11:
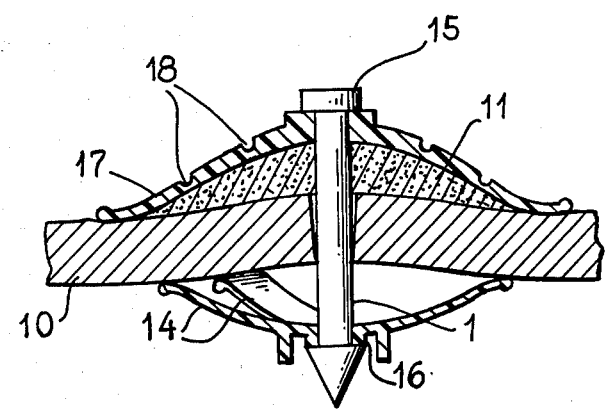
FIG. 11 is a diagrammatic view in section of an embodiment of the device of the invention in which the hollow dome is provided with two concentric grooves and the return piece is that represented in FIGS. 9 and 10.
Figure 12:
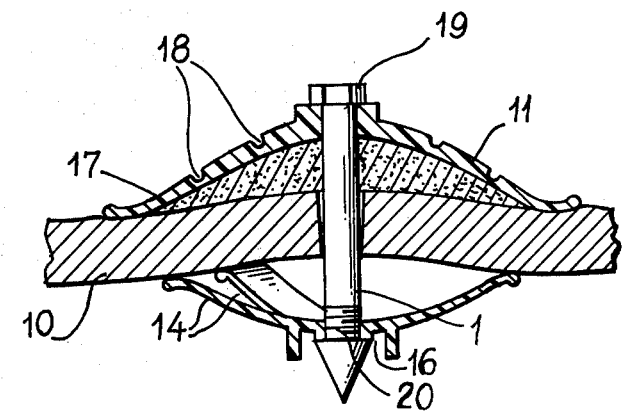
FIG. 12 is a diagrammatic view in section of an embodiment of the device of the present invention in which the hollow dome is provided with two concentric grooves, the return piece is that represented in FIGS. 9 and 10 and the fixing means is provided, at its end intended to be placed in the said return piece, with a thread and a head having the form of a hexahedron.
Figure 13:
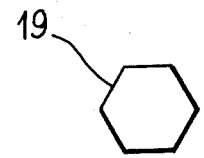
FIG. 13 is a diagrammatic view in projection of the end of the fixing means, called the head, made in the form of a hexahedron.
Figure 14:
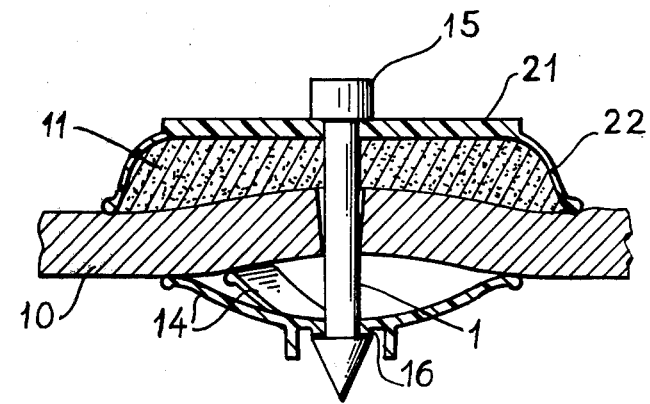
FIG. 14 is a diagrammatic view in section of an embodiment of the present device in which the hollow dome comprises a reduced area situated between its top and its rim. The return piece is that represented in FIGS. 9 and 10.
Figure 15:
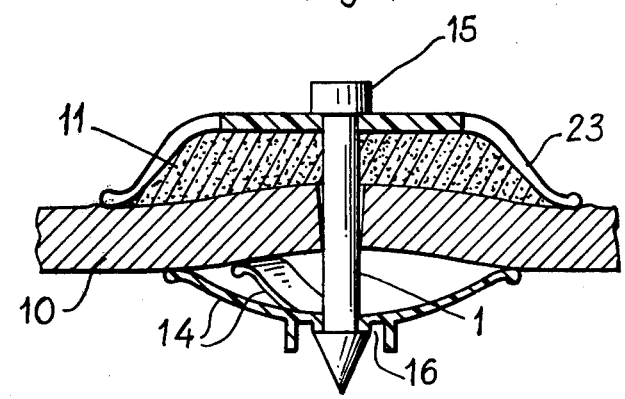
FIG. 15 is a diagrammatic view in section of an embodiment of the device of the present invention in which the hollow dome is partially cut out at its periphery; the return piece is that represented in FIGS. 9 and 10.
Figure 16:
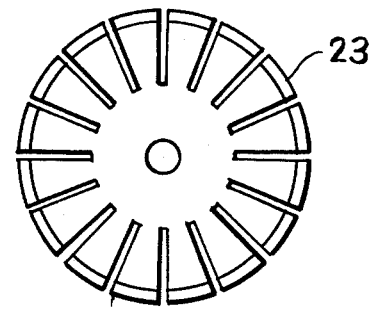
FIG. 16 is a diagrammatic view in projection of the hollow dome partially cut out at its periphery, represented in FIG. 15.

As already indicated FIGS. 1 to 16 illustrate a certain number of embodiments of the device which forms the subject of the invention.

Nevertheless, starting with the members described above it is possible to carry out numerous permutations both regarding the forms of these members and regarding the methods of making them up, their arrangement and their placing with respect to the skin of the ear of the subject, or to combine them in a very varied manner.

We claim:

1. A device for the cutaneous application of medicinal substances, comprising:
   an elastically deformable and generally cup-shaped cap having a medicinal substance therein;
   an elongated pin-like fastening member carried by said cap and extending from the bottom thereof outwardly past the rim of the cup-shaped cap; and
   a resilient retaining means for engaging and pulling on said fastening member to thereby pull the bottom of said cup-shaped cap toward a surface against which the rim of said cap is applied and through which said fastening member extends.

2. A device as defined in claim 1 wherein said fastening member is provided with threads at the end thereof which engages said retaining means, its opposite end being enlarged and in the form of a polyhedron.

3. A device as defined in claim 1 wherein the wall of said cup-shaped cap is provided with at least one concentric groove.

4. A device as defined in claim 1 wherein the wall of said cup-shaped cap is provided with cut-away portions at its periphery.

5. A device as defined in claim 1 wherein the wall of said cup-shaped cap is provided with at least one area of reduced thickness between its bottom and its rim.

* * * * *